United States Patent [19]

Hamel

[11] Patent Number: 4,470,294
[45] Date of Patent: Sep. 11, 1984

[54] METHOD AND APPARATUS FOR SIMULTANEOUS DETERMINATION OF FLUID MASS FLOW RATE, MEAN VELOCITY AND DENSITY

[75] Inventor: William R. Hamel, Farragut, Tenn.

[73] Assignee: The United States of America as represented by the United States Department of Energy, Washington, D.C.

[21] Appl. No.: 433,299

[22] Filed: Oct. 7, 1982

[51] Int. Cl.$^3$ .......................... G01N 9/00; G01F 1/86
[52] U.S. Cl. .................................. 73/32 A; 73/861.37
[58] Field of Search ...................... 73/861.37, 32 A, 59

[56] References Cited

U.S. PATENT DOCUMENTS 3,080,750  3/1963  Wiley ............................... 73/861.37
3,261,205  7/1966  Sipin ................................. 73/861.37
3,608,374  9/1971  Miller ............................. 73/32 A X

OTHER PUBLICATIONS

*Report on Blood Flow Measurement,* phase 1 report, A. J. Sipin, Apr. 1964, pp. 1–9.

*Primary Examiner*—Stephen A. Kreitman
*Assistant Examiner*—Vincent P. Kovalick
*Attorney, Agent, or Firm*—Fred O. Lewis; Stephen D. Hamel; Michael F. Esposito

[57] ABSTRACT

This invention relates to a new method and new apparatus for determining fluid mass flowrate and density. In one aspect of the invention, the fluid is passed through a straight cantilevered tube in which transient oscillation has been induced, thus generating Coriolis damping forces on the tube. The decay rate and frequency of the resulting damped oscillation are measured, and the fluid mass flowrate and density are determined therefrom. In another aspect of the invention, the fluid is passed through the cantilevered tube while an electrically powered device imparts steady-state harmonic excitation to the tube. This generates Coriolis tube-damping forces which are dependent on the mass flowrate of the fluid. Means are provided to respond to incipient flow-induced changes in the amplitude of vibration by changing the power input to the excitation device as required to sustain the original amplitude of vibration. The fluid mass flowrate and density are determined from the required change in power input. The invention provides stable, rapid, and accurate measurements. It does not require bending of the fluid flow.

4 Claims, 5 Drawing Figures

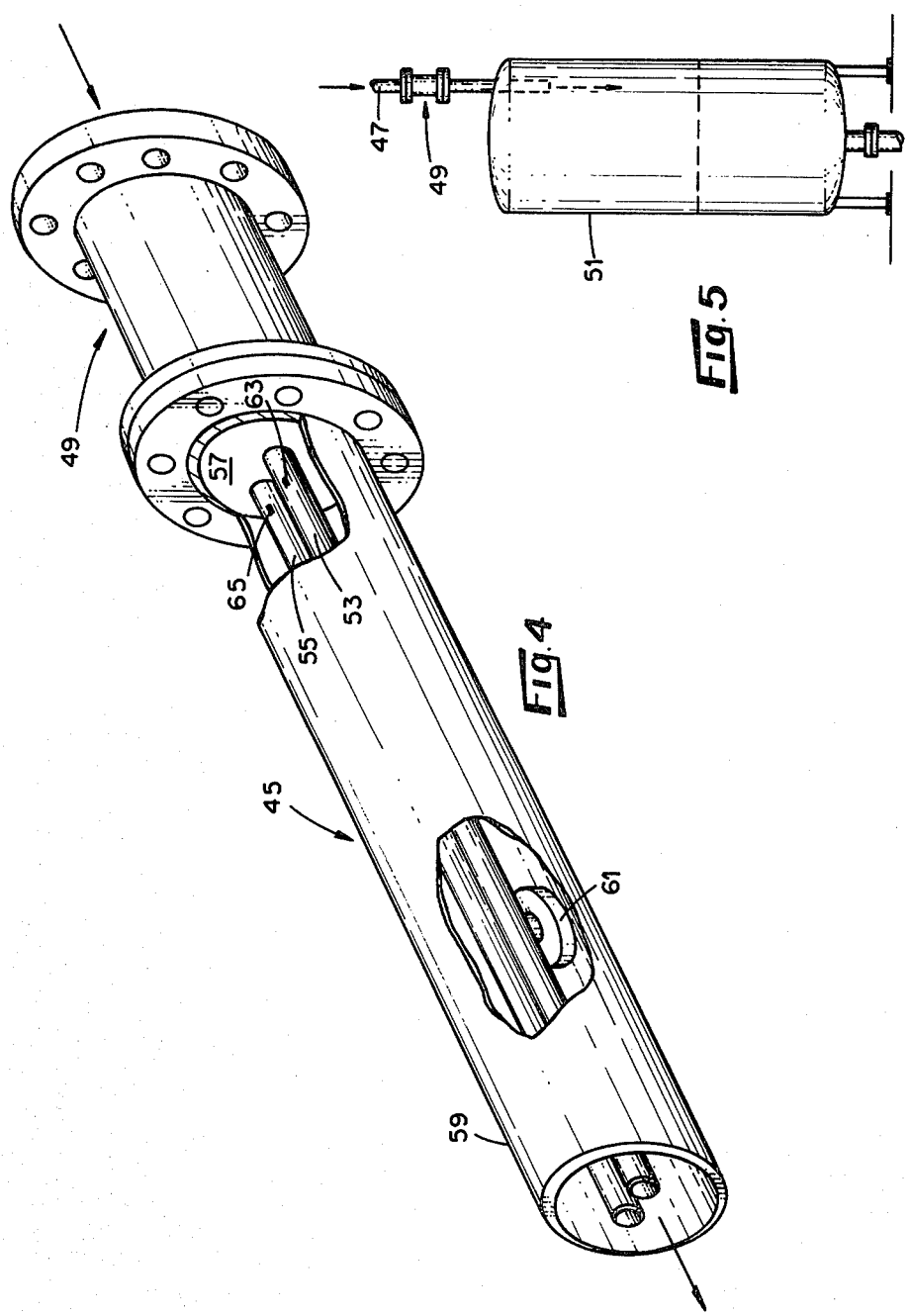

METHOD AND APPARATUS FOR SIMULTANEOUS DETERMINATION OF FLUID MASS FLOW RATE, MEAN VELOCITY AND DENSITY

BACKGROUND OF THE INVENTION

This invention relates generally to methods and apparatus for the determination of fluid density, mass flowrates, and mean velocity. More particularly, it relates to measuring such parameters by subjecting a stream of the fluid of interest to Coriolis inertial reaction forces. As used herein, the term "fluid" includes not only homogeneous gases and liquids but also slurries, fluidized particles, and the like. The invention was made as a result of a contract with the U.S. Department of Energy.

The state of the art for mass flowmeters of the Coriolis type is described in the following publications, both of which are incorporated herein by refernece: K. O. Plache, "Coriolis/Gyroscopic Flow Meter", *Mech. Eng.*, March 1979, pp. 36–41; W. R. Hamel, "Analysis of Cantilever Coriolis Mass Flowmeter Concept", (Dissertion; December, 1981), University of Tennessee, Knoxville, Tenn. Mass flowmeters of the Coriolis type are disclosed in the following patents to James E. Smith: U.S. Pat. No. 4,109,524, issued Aug. 29, 1978, and U.S. Pat. No. 4,187,721, issued on Feb. 12, 1980.

Previous flowmeters of the Coriolis type have not been entirely satisfactory because of instability, mechanical complexity, or susceptibility to erosion by the fluid being measured.

SUMMARY OF THE INVENTION

Accordingly, it is an object of this invention to provide a novel method and novel apparatus for directly determining fluid density and mass flowrates.

It is another object to provide a Coriolis flowmeter which is relatively insensitive to changes in environmental conditions, such as temperature.

It is another object to provide an accurate Coriolis flowmeter which is characterized by straight-through fluid flow.

Other objects and advantages will be made evident hereinafter.

In one aspect, the invention is a new flowmetering method in which a fluid is passed through a novel Coriolis-type flowmeter comprising a cantilevered tube which is subjected to static-deflection excitation. It has been found that the dynamic response of the cantilivered tube is essentially a second-order damped response in which the decay constant and frequency of vibration are dependent on the fluid density and frequency of vibration, respectively. In accordance with the invention, the decay constant and frequency of the damped response are measured. These values then are used to compute the fluid mass flowrate and density. The mean velocity of the fluid can be determined from the cross-sectional area of the tube and the flowrate and density.

In another aspect, the invention is a method in which fluid is passed through the cantilevered tube while an electrically powered forcing device imparts steady-state harmonic excitation to the tube, vibrating it at a selected frequency and amplitude. This subjects the particles of fluid to harmonic angular velocity and generates Coriolis damping forces acting on the tube. Means are provided to respond to incipient flow-induced changes in the amplitude of vibration by changing the power input to the forcing device as required to sustain the original amplitude of vibration. The fluid mass flow rate and density then are determined from the required change in power input.

BRIEF DESCRIPTION OF THE DRAWINGS

FIG. 4 is a perspective view, partly in cutaway, of a dual-tube flow sensor designed in accordance with the invention, and FIG. 5 is a schematic diagram showing the sensor (FIG. 4) as mounted to discharge slurry into the headspace of a slurry receiver.

DETAILED DESCRIPTION OF THE INVENTION

Figure 1:
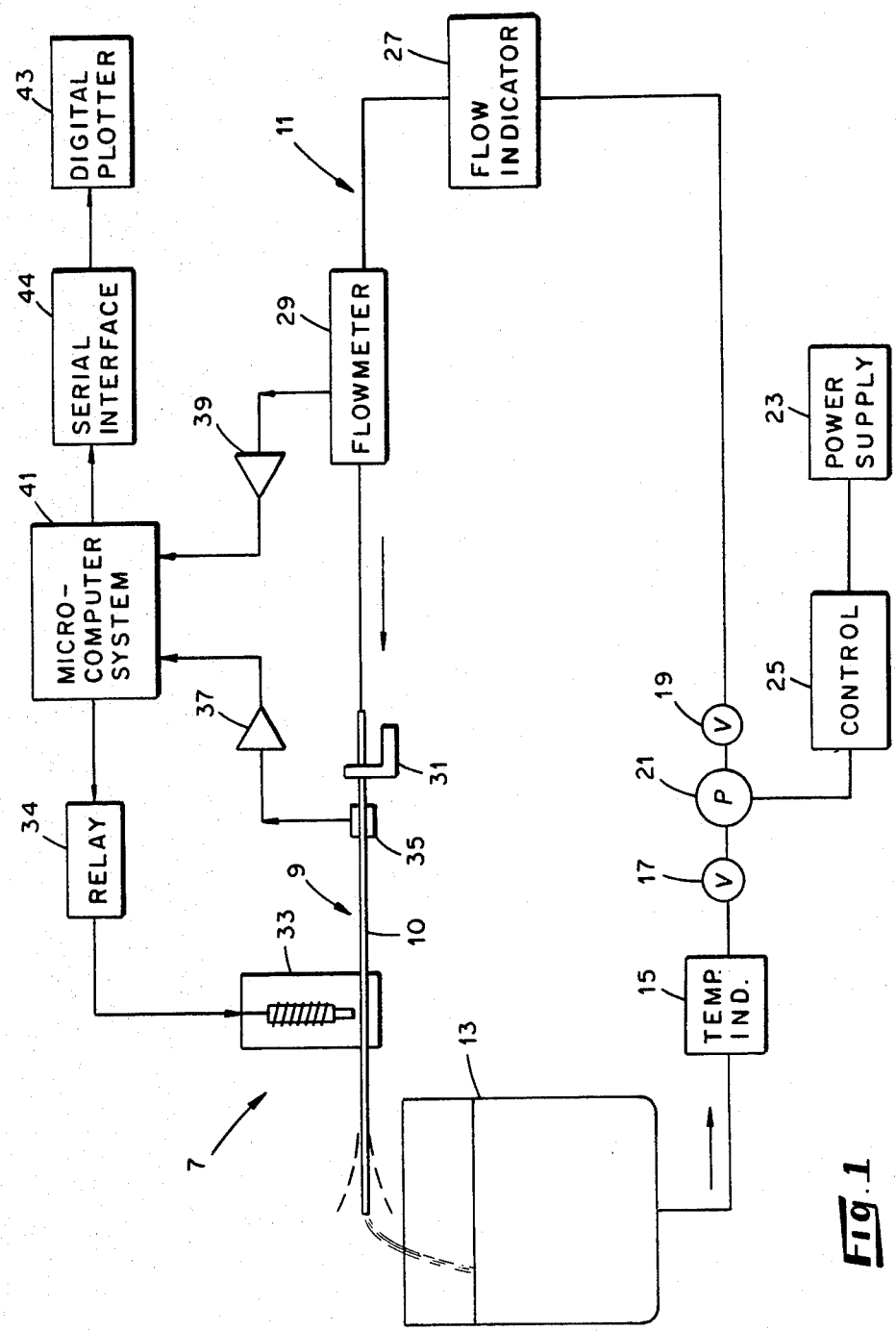
FIG. 1 is a schematic diagram of an experimental flowmetering system designed in accordance with the invention.

Referring to FIG. 1, the invention will be illustrated as utilized in an experimental system 7 designed to display the mass flowrate, density, and mean velocity of a stream of water. The system included a special flow-sensor tube 9, which was designed and operated in accordance with the invention. The remainder of the system consisted of conventional components. As shown, the sensor 9 was incorporated in a flow loop 11 through which the water was circulated. The loop also included a water reservoir 13, a temperature indicator 15, block valves 17 and 19, a centrifugal pump 21, a power supply 23 and Variac control 25 for the pump, a flow indicator 27, and a standard thermal flowmeter 29 connected to discharge into an end of the sensor 9. The thermal flowmeter produced an electrical output proportional to the mass flowrate therethrough.

In accordance with the invention, the special flow sensor was a straight tube having a cantilevered portion 10. The cantilevered tube was composed of stainless steel and had a length of 50.17 cm, an outside diameter of 9.25 mm, and an inside diameter of 7.5 mm. One end of the tube was rigidly supported by a bracket 31 and connected to receive fluid from the thermal flowmeter 29. The remainder of the tube was unencumbered, so that it might be vibrated. The outlet end of the tube extended into the headspace above the water in the reservoir 13. As shown, an A.C. solenoid 33 was mounted adjacent to the canilevered tube to effect static-deflection motion excitation of the same. That is, when energized, the solenoid plunger contacted the portion 10 and deflected it a selected distance (e.g., one cm) from its normal axial position. When de-energized, the solenoid released portion 10, initiating transient, uniplanar vibration thereof. The solenoid was actuated by a solid-state relay 34.

Still referring to FIG. 1, a four-arm strain-gage bridge 35 was mounted on the tube 10 as shown to generate an electrical output proportional to the magnitude of the vibrations of the tube with respect to time. As shown, the outputs from the bridge 35 and thermal flowmeter 29 were fed to amplifiers 37 and 39, respectively. The amplifier outputs were fed into a realtime micr computer system 41 (Model LSI-11, Digital Equipment Co.,), which was programmed to (a) intermittently excite transient vibration of the flow sensor 9, (b) record and store tube-deflection data and thermal flowmeter data; and (c) perform calibration- and flow-measurement algorithm calculations. As shown, the microcomputer system generated an output for operating the relay 34. The system also generated outputs respectively proportional to the mass flowrate and density of the water in loop 11; these outputs were fed to a digital plotter 43 via s serial interface 44. The system 41 included a programmable realtime clock for providing precision date-sampling intervals.

In a typical operation of the system shown in FIG. 1, it was first determined that the damped vibration of the sensor 9 was unimodal through 250 Hz. The values for certain calibration constants (to be described) were then determined, using the thermal flowmeter 29 as a secondary standard. The water flow through the loop 11 then was set at ten different values within a flow range of 20:1, and the statistical averages and standard deviations were calculated for the constants. With these constants stored in the microcomputer system, water was circulated through the loop 11 at various rates, and the mass flowrate diplays for the cantilevered sensor were compared with the mass flowrates determined with the thermal flowmeter. The typical flowrate measurement involved establishing about 1000 data points relating to the vibration-decay curve for the vibrating sensor tube; this required less than 0.5 sec.

Figure 2:
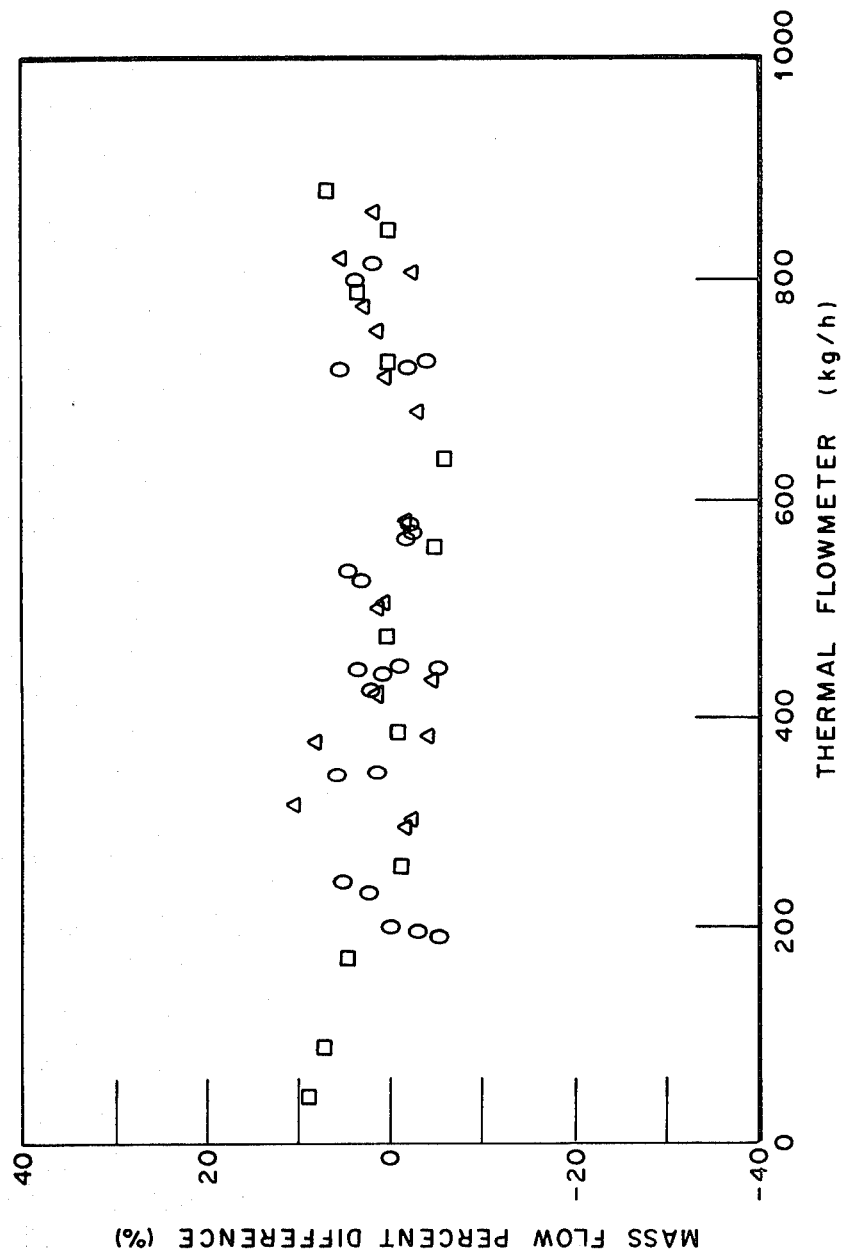
FIG. 2 is a graphical mass-flow regression comparison of a conventional thermal mass flowmeter and a cantilevered mass flowmeter designed in accordance with the invention.
Figure 3:
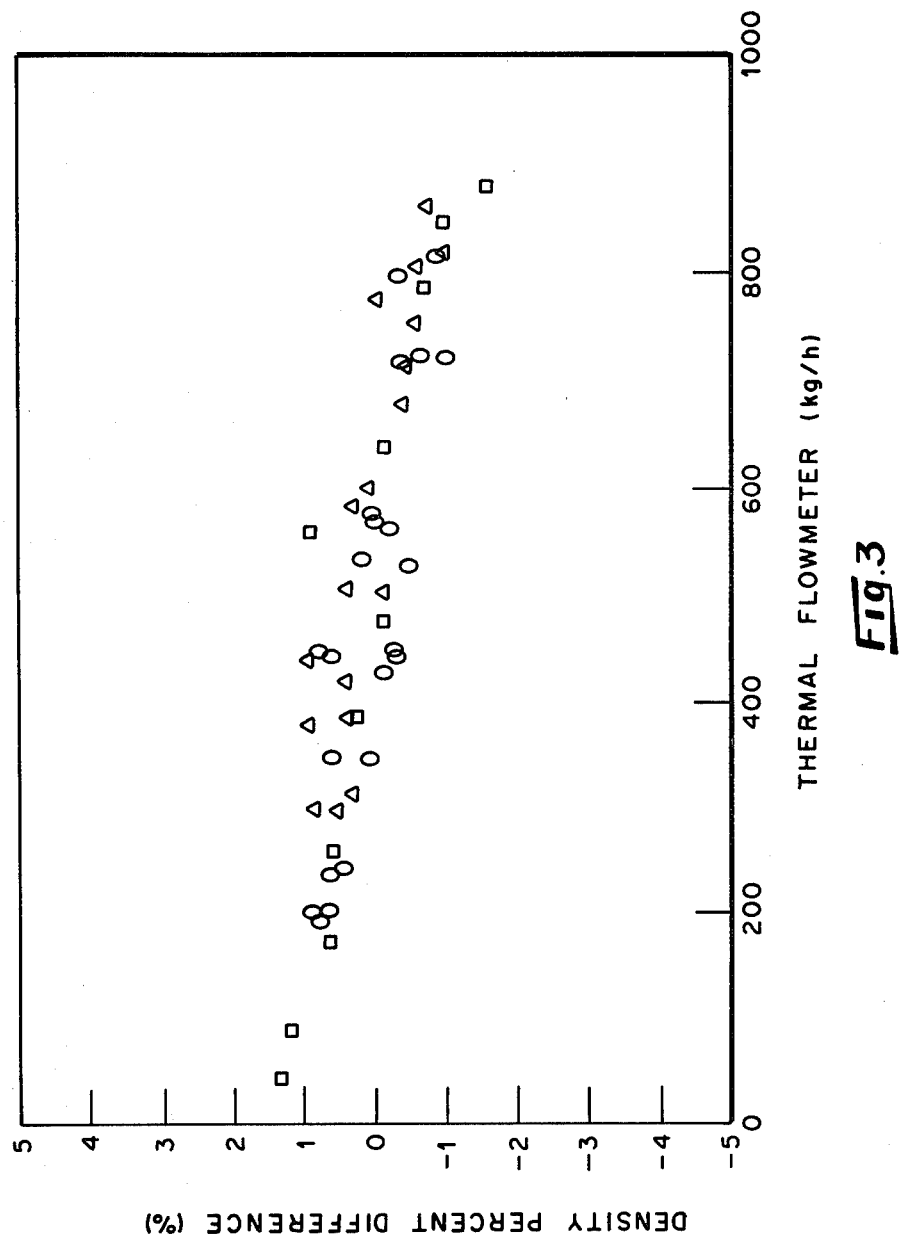
FIG. 3 is a graph in which the percent difference between (a) the density of water as calculated in accordance with the invention and (b) the known density of water is plotted as a function of mass flowrates as determined with a standard thermal flowmeter.

FIG. 2 compares mass flowrate determinations made with the thermal flowmeter 29 and cantilevered sensor 9 for three separate test scans. The mass-flow-percent difference is a plot of the variation of the experimental cantilever Coriolis flowmeter and the thermal flowmeter coincident readings about a linear regression line through the entire set of readings. This plot demonstrates the relative agreement between the two flowmeters. If they were in perfect agreement, all of the data would fall on the zero-line over the range of thermal flowmeter readings. As shown, the difference is within ±10% over the full range of measurement. These results are of the order of the thermal flowmeter itself. It is not possible from this relative comparison to determine how much of the ±10% was due to either one of the meters. FIG. 3 is a similar showing relating to the density of water and presents the percent difference between the density valves determined in accordance with the invention and the known density of water (997 kg/cm$^3$), plotted as a function of the thermal flowmeter output. The density values based on data obtained with the canilevered tube 9 are within ±2% of the known value over the full range of measurement.

Referring to system 7 (FIG. 1), when fluid is passed through the flow sensor 9 while the latter is vibrating in the transient mode, the angular velocity of the tube and the linear velocity of the fluid particles relative to the tube combine to generate Coriolis inertial forces which damp the vibrations of the tube. I have found that the decay rate of the damped vibration is related to the fluid mass flowrate and that the frequency of the vibration is strongly related to fluid density and less strongly related to fluid velocity. I have also found that the density ($\rho$), mean velocity (U), and mass flowrate ($\dot{m}$) of the fluid may be determined by means of algorithms related to the decay rate and the frequency of the damped vibrations. The values for $\rho$, U, and $\dot{m}$ may be determined by means of the following algorithms:

$$(1 - \beta) = \frac{R_2 + R_1^2}{R_{C2}} \qquad a_2 \beta U = R_1 - (1 - \beta) R_{C1}$$

$$\rho = \frac{a_1 (\beta)}{(1 - \beta)} \quad U = \frac{a_2 \beta U}{a_2 \beta} \quad \dot{m} = \left[ K_{\dot{m}} \frac{a_2 \beta U}{(1 - \beta)} \right]$$

where
 $R_1$ is the decay constant of the tube vibration.
 $R_2$ is the frequency of the tube vibration.
 $R_{C1}$ is the decay constant of the tube vibration with no fluid flowing (calibrated)
 $R_{C2}$ is the frequency of oscillation-squared of the tube vibration with no fluid flowing (calibrated).
 $K_{\dot{m}}$ is the calibration constant for the mass flowrate.
and where calibration constants $a_1$, $a_2$, and $K_{\dot{m}}$ may be calculated as follows, using the thermal flowmeter 29 as a secondary standard and knowing the density of water:

$$a_1 = \frac{\rho(1 - \beta)}{\beta} \quad a_2 = \frac{R_1 - (1 - \beta) R_{C1}}{U} \quad K_{\dot{m}} = \frac{\dot{m}_{secondary}(1 - \beta)}{a_2 \beta U}$$

The above-referenced dissertation gives the principles underlying these algorithms and presents examples of software for implementing the same. The cantilevered Coriolis meter provides mass flowmeter measurements which are independent of viscosity and pressure. Pressure pulsations and slugging associated with mass flow variations will be measured as an average over the length of the tube.

Tables I and II list various parameters and calibration-constant values for the above-described runs conducted in system 7.

TABLE I

| Parameter | |
|---|---|
| Sensor tube: | |
| Outside Diameter (mm) | 9.25 (0.375 in.) |
| Inside Diameter (mm) | 7.75 (0.305 in.) |
| *Length (cm) | 50.17 (19.75 in.) |
| *Empty Natural Frequency (Hz) | 30 |
| *External Damping Coefficient × 10 [(N-s)/m$^2$] | 40 [9 lbf-s] /ft$^{2)}$ |
| Nondimensional $\beta$ = M/(M = m) | 0.2 (*0.16) |
| Maximum Flow Conditions: | |
| *Volumetric flow rate (L/h) | 900 (4gpm) |
| Mean velocity (m/s) | 4.9 (16 ft/s) |
| Reynolds number | 41,500 |

*Measured values; other data are nominal values
; M,m represent masses of fluid and flow sensor tube 9, respectively, per unit length

TABLE II

| Calibration parameter | Mean | Standard Division (% of mean) |
|---|---|---|
| Channel Biases: | | |
| Thermal Flowmeter (kg/h) | 2.95098 | |
| Cantilever Deflection with flow (V) | −0.03180 | |
| empty (V) | 0.12604 | |
| Calibration Constants: | | |
| Empty decay constant, $R_{Cl}$ (s$^{-1}$) | 1.070393 | 3.98 |
| Empty frequency-squared $R_{Cl}$ (s$^{-2}$) | 35,495.9 | 0.28 |
| $a_1$ | 318.5714 | 0.52 |
| $a_2$ | 6.851901 | 3.08 |

FIGS. 4 and 5 depict another embodiment of a cantilevered-tube flowmeter designed in accordance with the invention. The flowmeter assembly, designated as 45, includes a protective housing 59, which is flanged at its inlet end for connection to a tubular coupling 49. The coupling is connected to a process line 47 to receive slurry therefrom. The other end of the housing extends into the headspace of a slurry receiver 51. As shown, the housing contains identical, cantilevered tubes 53 and 55, which are rigidly supported by a plate 57 closing an end of the housing. Tube 53 serves as a flow sensor and extends through the plate to receive process fluid from the coupling. Tube 55 is not in communication with the coupling and serves as an empty reference type.

As shown, the housing 59 contains an electromagnet 61 for simultaneously inducing transient vibration in the tubes; that is, the tubes are deflected a selected amount by magnetic and then released to vibrate freely. The tubes carry respective vibration-detection means 63 and 65 for generating electrical outputs proportional to the magnitude of the tube vibrations with respect to time. These outputs are fed to conventional computer means for operating the electromagnet 61, storing tube-deflection data, and performing the above-mentioned algorithm calculations. The reference tube 55 is exposed to the same environment as tube 53 but is not subject to Coriolis damping forces. The output from the reference tube is fed into the computer and used to standardize the metering system with regard to environmental effects. Thus, at all time the metering system is free from environment-induced instabilities. This embodiment of the flowmeter may be sized to permit use of the algorithms presented above.

In another form of the invention, the fluid of interest is passed through a cantilevered sensor tube (e.g., tube 9, FIG. 1) while an electrically powered forcing device (e.g., an electromagnetic actuator) imparts steady-state harmonic excitation to the tube, vibrating it a selected fixed frequency and amplitude. The particles of the fluid are subjected to harmonic angular velocity and generate Coriolis damping forces which act on the tube. Means are provided to respond to incipient changes in the amplitude of vibration by changing the power input to the forcing device as required to sustain the original amplitude of vibration. The mass flowrate then can be determined from the required change in power input. This mode of operation is based on my finding that the power input required to sustain the vibration is proportional to the rate of change of work done by the damping forces, which are dependent on mass flowrate. In a system of the kind just described, a conventional servo-control arrangement would be used to vary the power input in response to sensed changes in the amplitude of vibration. The electrical level of the servo-controller output would be related to total tube damping and hence flow rate. The system for adjusting the power input to the forcing device may be similar to that described in the above-referenced article by Plache. Because this form of the invention utilizes steady-state excitation of the cantilevered sensor, the algorithms for calibration and measurement will differ from those presented above.

The foregoing description of the invention has been presented for illustrative purposes and to enable others skilled in the art to utilize the invention in various embodiments and with various modifications suited to a particular use. It will be understood that the illustrated form of the invention is not necessarily the optimum. Obviously, many modifications and variations are possible in light of the teaching herein. It is intended that the scope of the invention be defined by the appended claims.

What is claimed is:

1. A method of measuring fluid mass flowrate and density, said method comprising:
   providing a straight cantilevered tube,
   passing a fluid through said tube,
   exciting the fluid-traversed tube to induce transient oscillation thereof, thus applying harmonic angular velocity to the fluid particles therein and generating Coriolis forces which act on said tube to damp the oscillation thereof,
   measuring the frequency and decay constant of the damped transient oscillation, and
   calculating the fluid mass flowrate and density from said frequency and decay constant.

2. A method of measuring fluid mass flowrate, said method comprising:
   providing a straight cantilevered tube,
   passing a fluid through said tube from its cantilevered end to its unsupported end,
   exciting the fluid-traversed tube to induce transient oscillation thereof, thus applying harmonic angular velocity to the fluid particles therein and generating Coriolis forces which act on said tube to damp the oscillation thereof,
   measuring the frequency and decay constant of the damped transient oscillation, and calculating the fluid mass flowrate from said frequency and decay constant.

3. A device for measuring the mass flow rate and density of a fluid, comprising:
   a straight, cantilevered tube having a fixed end portion disposed to receive said fluid and a freely vibratable end portion through which said fluid is discharged;
   actuating means for deflecting said tube when traversed by said fluid to induce transient oscillation at the natural resonant frequency thereof, thereby applying harmonic angular velocity to the fluid particles traversing said tube and generating Coriolis forces which act on said tube to provide damped transient oscillation thereof; and
   means for measuring the frequency and decay constant of said damped transient oscillation of said tube and calculating the fluid mass flowrate and density from the measured values of frequency and decay constant.

4. The device of claim 3 further comprising:
   an empty, straight, cantilevered reference tube having a fixed end portion and a freely vibratable end portion and wherein said actuating means includes means for deflecting said reference tube to induce transient oscillation thereof and said measuring and calculating means includes means for measuring the transient oscillation of said reference tube to calibrate said device.

* * * * *